United States Patent [19]
Arnold et al.

[11] Patent Number: 5,766,424
[45] Date of Patent: Jun. 16, 1998

[54] PROCESS FOR REMOVING TRIOXANE FROM AN AQUEOUS MIXTURE

[75] Inventors: Dieter Arnold, Königstein; Bernhard Hierholzer, Frankfurt; Karl-Friedrich Mück, Wiesbaden; Monika Reiss, Schwalbach; Peter Richter, Waldems-Bermbach; Hans-Dietmar Schnabel, Eppstein; Hubert Wloch, Niedernhausen, all of Germany

[73] Assignee: Hoechst Aktiengesellschaft, Frankfurt, Germany

[21] Appl. No.: 683,748

[22] Filed: Jul. 17, 1996

[30] Foreign Application Priority Data

Jul. 19, 1995 [DE] Germany ............... 195 26 307.3

[51] Int. Cl.⁶ .............. B01D 3/00; C07D 323/06
[52] U.S. Cl. .................. 203/74; 203/77; 203/80; 549/368
[58] Field of Search ............... 203/14, 17, 74, 203/73, 77, 80, 99, DIG. 19; 549/368

[56] References Cited

U.S. PATENT DOCUMENTS 5,061,349  10/1991  Küppenbender et al. ............... 203/14

FOREIGN PATENT DOCUMENTS

| 0133669 | 3/1985 | European Pat. Off. . |
| 0304499 | 3/1989 | European Pat. Off. . |
| 0596381 | 5/1994 | European Pat. Off. . |
| 0692481 | 1/1996 | European Pat. Off. . |

OTHER PUBLICATIONS

JP 363162686A Abstract.

JP 35919688A Abstract.

JP 35817437A Abstract.

Primary Examiner—Virginia Manoharan
Attorney, Agent, or Firm—Frommer Lawrence & Haug LLP

[57] ABSTRACT

A process for removing trioxane from a liquid mixture containing trioxane, water and formaldehyde, which includes distilling the liquid mixture in a first distillation stage at a low pressure, distilling the resulting distillate in a second distillation stage at a higher pressure and taking off trioxane as bottom product.

10 Claims, 1 Drawing Sheet

PROCESS FOR REMOVING TRIOXANE FROM AN AQUEOUS MIXTURE

The invention relates to a process for preparing trioxane from a liquid mixture containing trioxane, water and formaldehyde.

On an industrial scale (according to Ullmann, Volume A 11 (1988), p. 645), trioxane is produced in a multistage process in which formaldehyde is trimerized in aqueous solution using a catalyst and the resulting reaction mixture is worked up. The mixture of trioxane, water and formaldehyde, which also contains by-products, is extracted with methylene chloride or another water-immiscible solvent such as ethylene chloride or benzene. In a subsequent distillation, the solvent is recovered and recycled to the extractive distillation. This process requires large amounts of solvent, which must be recovered with high expenditure of energy. Emissions arising must be disposed of in a complex manner, since methylene chloride and benzene are classified as hazardous pollutants.

The object therefore underlying the invention was to provide a process which succeeds without solvent.

According to the invention the object is achieved by distilling the liquid mixture in a first distillation stage at a low pressure, distilling the resulting distillate in a second distillation stage at a higher pressure and taking off trioxane as bottom product.

The invention thus relates to a process for removing trioxane from a liquid mixture containing trioxane, water and formaldehyde, which comprises distilling the liquid mixture in a first distillation stage at a low pressure, distilling the resulting distillate in a second distillation stage at a higher pressure and taking off trioxane as bottom product. In this process the ternary azeotrope formaldehyde, trioxane, water is overcome and it is possible to obtain virtually pure trioxane.

The process is preferably carried out at absolute pressures of 0.1 to 20 bar. Preferably, the range is from 0.2 to 10 bar, particularly preferably a low pressure is in the range from 0.1 to 2 bar and a higher pressure in the range from 2 to 20 bar and very particularly expediently, a low pressure is about 0.5 bar and a higher pressure about 6 bar.

The invention is made possible by the surprising discovery that the ternary azeotrope formaldehyde/trioxane/water is displaced, by pressure elevation, in a manner expedient according to the invention.

The invention further relates to a process for preparing trioxane, in which formaldehyde is trimerized in aqueous solution using a catalyst and the resulting liquid mixture is worked up, which comprises distilling the liquid mixture in a first distillation stage at a low pressure, distilling the resulting distillate in a second distillation stage at a higher pressure and taking off trioxane as bottom product.

The advantages of the processes of the invention are essentially that solvent is no longer necessary, thus the emission problem is solved and the entire process procedure is simplified, with a considerable reduction in operating costs and capital expenditure. The trioxane obtained is suitable as disinfectant and for preparing polyoxymethylenes or polyhydric alcohols.

The process of the present invention is described in more detail below with reference to a possible embodiment which is depicted as a flow diagram in the Figure.

DESCRIPTION OF THE PREFERRED EMBODIMENT

Figure 1:
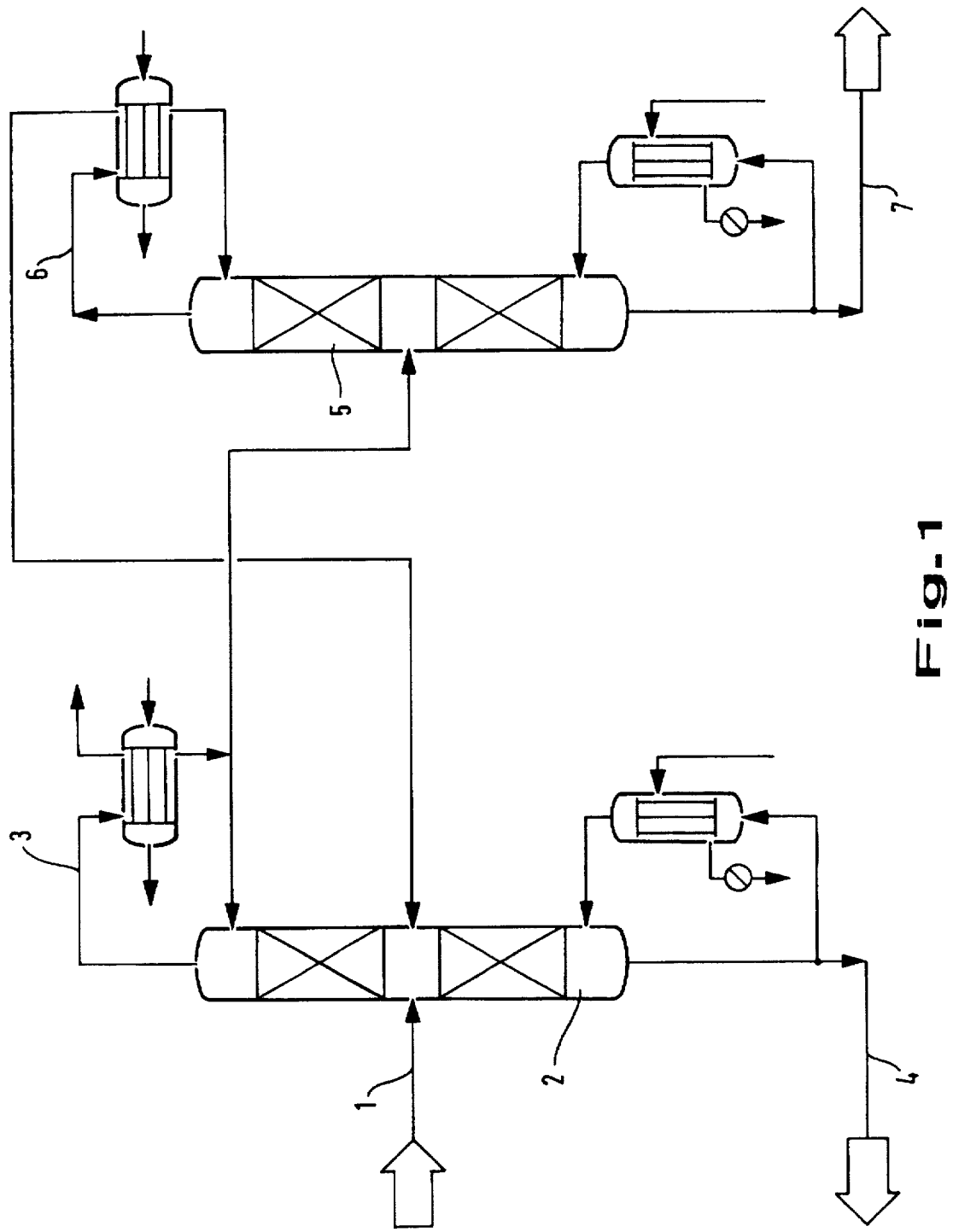
FIG. 1 shows a flow diagram depicting the process for removing trioxane from an aqueous mixture.

A liquid mixture 1 containig trioxane, water and formaldehyde is fed to a distillation column 2, preferably in the central area and is fractionated at a low pressure into a distillate 3 and a bottom product 4 which is depleted in trioxane. In a downstream column 5, whose central area is connected to the top of the column 2, the distillate 3 from the column 2 is separated at a higher pressure into a distillate 6 and a bottom product 7 which essentially comprises pure trioxane. The trioxane-depleted distillate 6 is recycled to column 2, preferably into its central area.

The process is explained further in the following example.

A stream of an aqueous mixture 1, essentially comprising 20% (by weight) of trioxane (TOX), 50% of formaldehyde (FOH) and 30% of water ($H_2O$) was treated in a plant in accordance with the flow diagram. The low pressure in column 2 was about 0.5 bar, the higher pressure in column 5 was about 6 bar. An analysis of the individual streams gave the following concentrations (% by weight):

|  | TOX | FOH | $H_2O$ | Comment |
| --- | --- | --- | --- | --- |
| Distillate 3 | 72.0 | 6.3 | 21.7 | ternary azeotrope at 0.5 bar |
| Bottom product 4 | 0.2 | 59.1 | 40.7 | |
| Distillate 6 | 60 | 9.2 | 30.8 | ternary azeotrope at 6 bar |
| Bottom product 7 | ~100% | | | virtually pure TOX |

We claim:

1. Process for removing trioxane from a liquid mixture containing trioxane, water and formaldehyde, which comprises distilling the liquid mixture in a first distillation stage at a low pressure, distilling the resulting distillate in a second distillation stage at a higher pressure and taking off trioxane as bottom product.

2. The process as claimed in claim 1, wherein the process is carried out at an absolute pressure of 0.1 to 20 bar.

3. The process as claimed in claim 1, wherein the process is carried out at an absolute pressure of from 0.2 to 10 bar.

4. The process as claimed in claim 1, wherein the low pressure is in the range from 0.1 to 2 bar (absolute).

5. The process as claimed in claim 1, wherein the higher pressure is in the range from 2 to 20 bar (absolute).

6. The process as claimed in claim 1, wherein the low pressure is about 0.5 bar (absolute).

7. The process as claimed in claim 1, wherein the higher pressure is about 6 bar (absolute).

8. The process as claimed in claim 1, wherein the trioxane can be used as a disinfectant or used for preparing polyoxymethylenes or polyhydric alcohols.

9. The process as claimed in claim 1, wherein the distillation stages are performed in two distillation columns connected in series, each distillation column having a top and a central area, the top of the first distillation column is connected to the central area of the second distillation column and the top of the second distillation column is connected to the central area of the first distillation column.

10. A process for preparing trioxane, in which formaldehyde is trimerized in aqueous solution using a catalyst and the resulting liquid mixture is worked up, which comprises distilling the liquid mixture in a first distillation stage at a low pressure, distilling the resulting distillate in a second distillation stage at a higher pressure and taking off trioxane as bottom product.

* * * * *